United States Patent
Hill

(10) Patent No.: US 9,092,014 B2
(45) Date of Patent: Jul. 28, 2015

(54) MULTI-EVENT TIME AND DATA TRACKING DEVICE

(71) Applicant: Roxanne Hill, Tappan, NY (US)

(72) Inventor: Roxanne Hill, Tappan, NY (US)

( * ) Notice: Subject to any disclaimer, the term of this patent is extended or adjusted under 35 U.S.C. 154(b) by 0 days.

(21) Appl. No.: 14/138,000

(22) Filed: Dec. 20, 2013

(65) Prior Publication Data

US 2014/0198623 A1  Jul. 17, 2014

Related U.S. Application Data

(60) Provisional application No. 61/739,863, filed on Dec. 20, 2012.

(51) Int. Cl.
| | | |
|---|---|---|
| G04G 11/00 | (2006.01) | |
| G04B 47/00 | (2006.01) | |
| G04G 13/02 | (2006.01) | |
| A61B 5/00 | (2006.01) | |
| G04F 1/00 | (2006.01) | |
| G06F 19/00 | (2011.01) | |

(52) U.S. Cl.
CPC ................ G04G 11/00 (2013.01); G04B 47/00 (2013.01); G04G 13/026 (2013.01); *A61B 5/00* (2013.01); *G04F 1/005* (2013.01); *G06F 19/32* (2013.01)

(58) Field of Classification Search
CPC ..... G04B 47/00; G04G 11/00; G04G 13/026; G04F 1/005; G06F 19/32; G06F 19/30; G06F 19/322; G06F 17/60
USPC ......... 368/10, 82, 96, 107–109, 46, 244, 250, 368/83, 84, 251; 340/309.4, 573.1; 708/131
See application file for complete search history.

(56) References Cited

U.S. PATENT DOCUMENTS

| | | | | |
|---|---|---|---|---|
| 5,400,012 | A * | 3/1995 | Walton | 340/573.1 |
| 5,691,932 | A * | 11/1997 | Reiner et al. | 368/10 |
| 6,314,405 | B1 * | 11/2001 | Richardson | 705/3 |
| 6,478,583 | B1 * | 11/2002 | Standiford et al. | 434/304 |
| 6,575,903 | B1 * | 6/2003 | Collins | 600/300 |
| 7,835,230 | B1 * | 11/2010 | Chang | 368/109 |
| 2004/0177101 | A1 * | 9/2004 | Underwood | 708/131 |
| 2005/0146988 | A1 * | 7/2005 | Dolson | 368/10 |
| 2005/0283327 | A1 * | 12/2005 | Bowman et al. | 702/81 |
| 2007/0047392 | A1 * | 3/2007 | Parkinson et al. | 368/108 |
| 2008/0157981 | A1 * | 7/2008 | Clair | 340/573.1 |
| 2009/0073813 | A1 * | 3/2009 | Stephens | 368/73 |
| 2009/0109798 | A1 * | 4/2009 | West et al. | 368/10 |
| 2010/0074058 | A1 * | 3/2010 | Campbell | 368/10 |
| 2011/0036801 | A1 * | 2/2011 | Krans et al. | 215/11.1 |
| 2013/0128704 | A1 * | 5/2013 | Khalil | 368/10 |

* cited by examiner

*Primary Examiner* — Amy Cohen Johnson
*Assistant Examiner* — Matthew Powell

(57) ABSTRACT

A battery operated multi-event data and time tracking device for monitoring baby care comprising a plurality of buttons on the face of the device, wherein buttons are brightly colored, illuminated and labeled with integers 1-12 as well as icons representing various baby care events. The buttons indicate the aggregate number of instances of a particular baby care event for a period of time, through the simultaneous illumination of integer buttons and a numeric display on an information screen. The information screen will additionally display various temporal and numerical data corresponding to particular baby care events. There is also a decimal point button, a clear button and scanning buttons as well as locking, alarm and lighting control switches. The device further comprises a microprocessor, a USB port, WiFi capability for data transfer to a permanent memory storage, wherein data will be organized in graphic format for the analysis of infant behaviors.

5 Claims, 3 Drawing Sheets

MULTI-EVENT TIME AND DATA TRACKING DEVICE

CROSS-REFERENCE TO RELATED APPLICATIONS

This nonprovisional patent application seeks to claim the benefit of priority, US and foreign, based on U.S. 61/739,863, a provisional patent application for a "Baby Care Time Tracking Device" filed on Dec. 20, 2012 with a Foreign Filing License granted on Jan. 3, 2013.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

This disclosure is related to the general field of time and data recording, retrieval and transfer, particularly related to baby care. This device is a direct-entry information collection, storage and retrieval device that provides a means to collect, store, organize and transfer relevant baby care event information as well as to provide alarm reminders at specific times or time intervals for selected events.

In the early months of an infant's life, doctors and caregivers monitor on a number of basic physiological events to ensure general health and to detect signs of illness. Much of the information necessary is provided by parents who are often too sleep-deprived and exhausted to record or recall important details, such as the duration, frequency and amount of various biological functions and infant behaviors including nursing, urination, bowel movements, sleep patterns among other baby care events. There is a need for data collection and tracking in the earlier years of a child's life, especially in the first year.

In U.S. Pat. No. 5,691,932, titled "Care Giver Data Collection and Reminder System", Reiner et al. teaches a device for collecting information and providing reminders for individual infants. The information includes feeding times, measurable amounts of consumption of liquids or food, vomiting, bowel movements, medications, injections or shots, first words, walking, growth chart, records and doctor's appointments, allergies, allergic reaction to medications and similar issues and events. The device also provides alarm reminders to the caregivers. Reminders can be provided for the next time for medication, feeding schedule, the next expected bowel movement or the next doctor appointments among other events.

In U.S. Pat. No. 6,188,311, titled "Maternity and Life Time Tracking Apparatus and Method of Use", Rothschild et al. teaches an electronic apparatus provided to keep track of events and experiences big and small during the life of the child. For example, the day and/or date of the child's birth, celebratory events, events that relate to milestones in the child's life and similar occurrences are recorded and displayed. The invention may be installed in a wristwatch, a key chain, a baby bottle, plush toy, notebook or similar small objects. It is portable, preferably small enough and light enough to be held in a person's hand.

In U.S. Pat. No. 6,314,405, titled "Medical Log Apparatus", Richardson et al. discloses an electronic, hand held, icon driven medical log that can be used by the elderly, children, disabled individuals as well as people with minimal computer skills. The medical log includes three sets of icons. It is used for keeping track the date, time, condition, progress and location of a patient's ailments. The required entries are entered into the medical log using appropriate icons and stored in the log for later retrieval.

In U.S. Pat. No. 6,886,139, titled "Method and Apparatus for Managing Infant Care", Liu et al provides a method and apparatus for the management of complex nutritional and health requirements of infants. The portable invention collects information and can manually or automatically configure various reminders for the caregiver's use when attending to the infant. The preferred embodiment is for product information used to manage infants' complex nutritional and health requirements.

In U.S. Pat. No. 6,891,779, titled "Portable Electronic Recorder and Method for Operating Same", Pornel teaches a portable electronic device for recording data on events during the conducting of clinical trials of medicaments or analysis of human behavior provided with means for emitting signals and having memory for storing the commands given to the device. The device is particularly suitable in studies carried out by the pharmaceutical industry. To this end, it distributes standardized information regarding time intervals to be complied when administering medicaments and regarding symptoms or events whose start, end and, if appropriate, intensity, are to be recorded. This data is transmitted to local centers and then to doctors or associates, who communicate them to the patients who have been selected for the clinical trials or for studies involving analysis of human behavior. The patients are instructed to comply with the dosage regimen of one or more medicaments and to record the start and end of the occurrence of a set of predetermined symptoms or particular events for periods that may last for up to several months.

In U.S. Pat. No. 7,522,477, titled "Multi-event Timer Device", Sheldon discloses a portable electronic device for timing infant-related biological functions such as feedings, naps and diaper changes. The device consists of four buttons on the face of the device next to a display with four corresponding timer readings. The buttons are labeled with symbols representing infant biological functions to facilitate universal usage. The device also comprises switches to lock and unlock the device, to turn the alarm sound on and off as well as to indicate which breast was last used to nurse. Also, there is a light button. The four timers are count-up timers to indicate the time since the last biological function. Alarms can be set in half hour intervals for each timer. When a timer button is pressed again after it has been started, the timer is reset and returns to zero. The device has no recording, retrieving or transferring of information capability.

The benefits of breastfeeding a baby are numerous and well known. Pediatricians and lactation consultants recommend that mothers nurse their infants up to the first year of life. Trends in feeding times and durations can be very helpful to mothers who are nursing and/or pumping as well as formula-feeding their babies. To build milk production, nursing mothers are advised to begin nursing and/or pumping eight to twelve times a day, with each feeding/pumping being at most two to three hours after the start of the last feeding/pumping. The duration and/or ounces of milk produced during nursing and pumping sessions, specific to which breast was last used, is also critical information for building and maintaining milk production. Often times, if a consistent nursing/pumping schedule is not kept up in the first few months or even later in the first year when infants begin to eat solid foods, a mother's milk production will decrease and may cease altogether. To help track relevant feeding/pumping information, the present invention provides brightly colored and illuminated number buttons from 1 through 12 to alert the mother to which number feeding/pumping is next. In addition, there is a number display on the information screen indicating the same information. Also, the device tracks other information integral to building and maintaining milk production. For example, the amount of time an infant nurses or a mother pumps from the beginning, not the end, of the last feeding is tracked. In addition, the total number of ounces the child has consumed by nursing and/or formula-feedings as well as a the amount of breast milk a mother has pumped for the day are all important information to a nursing mother.

Similarly, data about the duration and time of day of naps as well as a infant's total sleep time in a 24-hour period is important to ensure an infant is getting the pediatrician-recommended number of hours of sleep a day for his/her particular stage of development In addition, tracking changes or trends in nap times can help parents put their babies on healthier sleep schedules.

Parents of newborns will be advised to count the total number of urinations and bowel movements per day. These numbers, if they are not within what is considered a normal range, can indicate a serious medical problem and even threaten a newborn's survival in the first few weeks of life. Using the present invention, this information can be instantly retrieved at anytime with the push of a button.

In summary, as anyone who has ever cared for a newborn or young baby understands, recording the number of events in a particular category of baby care within a 24-hour period; the time of and since a previous event began and/or ended; its duration; as well as its quantity (if applicable) can be critical in maintaining an infant's health.

In addition to the typical baby care related information discussed above, parents often need to record other types of information if their infant is not well including but not limited to the reading of temperatures to detect fevers, the time and frequency of vomiting as well as durations of long periods of crying. All this information can assist a healthcare professional to diagnose and treat a medical problem as well as to advise the parents about how to care for their sick baby. For example, knowledge of trends of infant vomiting related to feedings can aid a doctor in diagnosing Gastroesophageal Reflux Disease (GERD). Similarly, trends about when and how long an infant cries can help rule out colic. Colic is often diagnosed between two weeks and four months of age and is commonly defined as episodes of sustained crying in a well-fed and dry infant which lasts for more than three hours a day for more than three days a week for over three weeks. Furthermore, trends in how long and when a baby cries in combination with information about sleep can also aid parents in sleep-training their babies or developing a sleep schedule.

It is important to note that as difficult as it is for sleep-deprived parents to record all the different kinds of information recommended to maintain the health of their baby, it may be even more difficult for those parents to organize this information in a coherent manner to discuss with their pediatrician during the minimum of nine well-visits infants are scheduled during the first 18 months of their lives as well as to quickly detect for themselves if there is a problem and to immediately contact their pediatrician. Unfortunately, for most babies, it is precisely this period of time in their lives when their parents often lack the clarity of mind to be able to record or organize anything in an intelligible manner. On the other hand, a much more manageable task for parents would be to push a few easily identified and/or illuminated buttons on a portable device in their hands, around their neck or propped next to them, which will not only record the critical numbers, quantities and times of various baby care events but will organize them in an easily understood graph or chart format to be viewed, printed and/or emailed.

There are other methods of direct-entry data collection, retrieval and organization available to parents today. There are applications (APPS) on phones and tablets which are designed to record, store and organize some or all of the same information this device records, however, these devices usually have touch screens which easily lend themselves to data entry errors and, therefore, are not a reliable option for a bleary-eyed exhausted parent. Furthermore, these portable devices are used for many other purposes and are not specifically dedicated to baby care. Subsequently, the phones and tablets containing the baby care applications are usually personal devices that travel with their owners and are, therefore, not convenient for the care of most babies, who often have more than one caregiver.

In U.S. Pat. No. 7,522,477, titled "Multi-event Timer Device", Sheldon discloses a "Multi-event Timer Device" portable electronic device, comprising of a light, lock and alarm function along with four timers, dedicated to timing infant-related biological functions such as feedings, naps and diaper changes. The device is very easy for parents to use. Its direct-entry design and function provides important information, such as the time since the last feeding, nap or diaper change and provides this information simultaneously on one display giving a parent instant access to the information. Although Sheldon's device offers helpful alarms and simultaneously displays four count-up timers labeled for various baby care events, it is essentially just a multiple timer device of which there are many on the market. Sheldon's timer does not provide parents with recordable and retrievable information to monitor their baby's continued development. The present invention provides the same information Sheldon's device does and much more, although not simultaneously displayed. So, with the slight effort of a button push when the device is in its Locked and inactive mode, a parent is provided with not only the time since the last input for a particular baby care event but also the chronological number of that event in a 24 hour period as displayed on the information screen next to the timer reading. When the device is unlocked, a parent can access even more specific information including running totals, duration and amounts for various baby care events. As it is presented, Sheldon's timing device has no recording, retrieving, organizing or transferring of data capability so the information that is available is very limited for a parent wishes to use the device to monitor the development of their infant.

On the other side of the spectrum, Reiner et al.'s "Care Giver Data Collection and Reminder System", U.S. Pat. No. 5,691,932, discloses a device which has a very wide scope for collecting information regarding infant care. Some of this information is irrelevant for parents of newborns and young infants and most of it is very difficult to input and retrieve. While the device collects some of the same comprehensive data as the present invention, such as times, amounts and totals for various baby care events, the focus of the information and manner in which the device functions, particularly its method of data entry, suggests it is unsuitable for use by typical parents of newborns or infants. In fact, Reiner et al states that the device was designed to track information to "assist the parents of children with special needs [or illnesses] in keeping very accurate information."

Reiner et al also asserts that the device is designed for universal use by parents, daycares or other caregivers of infants. Still, the manner in which the device functions compared to the present invention suggests otherwise. A representative example of how Reiner et al's device vastly differs from the device at hand is to examine a typical situation for a parent of a young infant. For instance, an exhausted and sleep-deprived mother of a newborn wakes up at 3:00 am to feed her baby a bottle and change his diaper containing both urine and a bowel movement, a common occurrence. To record the diaper change, the mother must first press the Mode button on the device four times then the Record button to record the bowel movement; then she must press the Mode button five times then the Record button to record the urination; and then she must press the Mode button one time and then the Record button to record the time of the feeding; then she must press the Mode button once again and then the Amount button and finally keep pressing the "+" and "−" buttons until the number of ounces the baby consumed is obtained and then the Record button to record that amount. In contrast, to record the same information with the present invention, the same mother would only have to slide the Lock switch to Unlock, press the urination button and the corresponding number button which will light up and be displayed on the screen along with the urination icon, then the bowel movement button and the corresponding number button which will light up and be displayed on the screen along with the bowel movement icon, then the bottle button and the corresponding number button which will light up and be displayed on the screen along with the bottle feeding icon. Then, the mother presses the OZ button and finally the 4 button, the decimal point button and the five button. That is a total of only 10 button pushes of specifically labeled and easily identifiable buttons dedicated to each separate function with the present invention compared to 24 button pushes of four generic buttons with Reiner et al's device. Therefore, not only is Reiner et al's device not intuitive or user-friendly for a parent but the possibility of data entry mistakes is also much greater with that device. Furthermore, when using the present invention, any mistakenly inputted data can be instantly cleared by pressing the Clear button.

Another example of how the present invention can be distinguished from Reiner et al's is that the Mode button needs to be pressed seven times just to access the single mode of Doctor appointments and that does not include the button pushing required to input data in that mode. One embodiment of the device even allows for the input of textual messages as well. This exemplifies not only how cumbersome data entry can be for a typical caregiver using Reiner et al's device but also shows the objective and broad scope of the health-related data the device aims to collect.

In another embodiment, Reiner et al's device allows for interfacing with a hospital computer. While the present invention could easily be used by hospitals and synched with their computers, this invention's primary objective is to make the lives of infants' parents a little less chaotic and a little more organized. Reiner et al also states that the device has the capacity to download information in an "intelligible" manner or a "data dump" without providing any further detail. In contrast, one of the major functions of the present invention is to have its downloaded information organized in charts and graphs, such as bar graphs, so that a parent can instantly see how their baby is progressing across several different domains of care in a single 24 hour time period as well as on a weekly/monthly basis. In addition, the computer program associated with the present invention will organize the collected information and graph it along with standard infant percentile charts so that a parent can see how their baby's development is progressing compared to other infants his/her age.

As of yet, the only small, portable and specifically dedicated method of comprehensively recording all pertinent infant care information in a format that is easily reviewed and accessible by a variety of caregivers is through handwritten form in a journal. The problems with this method are numerous and obvious to anyone who has attempted it. It can be difficult for tired caregivers to remember and to record data, especially during late night feedings and diaper changes, as well as cumbersome to a carry pen, journal and timing device with them at all times. Also, the journal method leaves all the organization of the information up to the parents, which requires more time and attention, something these parents do not have any to spare.

In contrast to other devices and methods of infant data collection and retrieval, this portable device allows a parent, through an intuitive method of direct-entry data collection, to track a few specific events that are most relevant to their newborn or infant's health. While the device has the ability to be synched or interfaced with a hospital computer to track particular babies' health in pediatric or maternity wards, its main objective is to collect, retrieve and organize information in a manner which would be particularly helpful to new parents who are advised to closely monitor various biological functions when they leave the hospital with their newborn babies. The data entry system is simple enough for even an exhausted parent of a young infant to accurately input or access information in the middle of the night.

However, it is important to note that the device's utility does not end when a child is toilet-trained and no longer nursed, bottle or baby food fed. The device has several baby care event categories that can be useful to parents throughout their child's life, particularly during times of illness. There are temperature, medication and vomiting buttons, which can assist parents in monitoring an illness and to not only verbally report the collected information to their pediatrician or emergency room doctor but also to print or email a copy of the pertinent graphed data.

BRIEF SUMMARY OF THE INVENTION

The present invention discloses an electronic device for tracking and storing time, duration, temperature, quantity, and the chronological number of events for weeks at a time. It allows for the direct-entry collection, retrieval, organization and transfer of the information. In addition, the collected information can be retrieved from the device itself for a period of time and/or downloaded, via USB transfer, or optionally, wireless or WiFi transfer, to a computer, tablet or phone through an application/program, which will organize the information into printable charts/graphs/tables for parents' peace of mind and suitable for dissemination to pediatricians. The electronic device comprises a backlit information screen and various brightly colored and backlit number buttons and baby care-related category buttons labeled with universal symbols that have corresponding icons on the information screen, to facilitate easy and direct data input. The electronic device is a battery-operated device preferably having a durable clip on the back thereof, which a caregiver can adjust to prop up the device on a table or flat surface, wear on his or her belt and/or fasten a comfortable cord/fabric to the device so that it can worn around a caregiver's neck to maximize portability.

The battery operated device for tracking baby care in the present invention, comprises: an information screen on the face of the device, displaying a default setting of the current date and time when inactive in the Lock mode. When any of the baby care event buttons are pressed in the Lock mode, the device will display the corresponding icon with the most recent inputted data for that particular event, including the running time since the last input as well as the chronological number of the event with the current 24 hour time period. In the Unlock mode or active mode, a caregiver can record information for the current baby care event or can access more specific information regarding past events for a particular baby care category. When a baby care event button is pressed in the Unlock mode, the corresponding icon is displayed on the information screen along with totals and other specific inputted data for earlier times and readings for that particular baby event. This information can be reviewed in chronological order by pressing the scan buttons in either direction.

The present invention also comprises four or more groups of buttons on the same face of the device, including a first group of buttons representing integers 1 through 12, which can be used for data entry as well as to indicate the time since the most recent inputted times, amounts, readings or administrations of for various baby care events, facilitated through the use of a backlight and corresponding number displayed on the information screen. There is also a Clear button to delete any inputting errors and a Decimal point button to input a temperature reading, partial amounts and ounces in the feeding/nursing/pumping modes or to serve as a colon when inputting specific times.

The device further comprises a second group of buttons, brightly colored and/or illuminated for easy identification, on the face of the device, labeled as baby feeding events, including nursing, pumping, bottle feeding and baby food feeding as well as separate L or R buttons to signify left or right breast in nursing or pumping modes.

The device further comprises a third group of buttons, brightly colored and/or illuminated for easy identification, on the same face of the device, labeled as baby care information, including wet and/or soiled diapers or symbols equivalent to wet and/or soiled diapers, sleeping or a symbol equivalent to a sleeping, crying or a symbol equivalent to crying, medication or a symbol equivalent to medication, vomiting or a symbol equivalent to vomiting, temperature or a symbol equivalent to temperature, generic event or a symbol equivalent to a generic event;

There is a fourth group of buttons serving as scan buttons to access and scroll through recorded information in any baby care event category.

This electronic baby care tracking device further comprises an Alarm mode, accessed by a small switch/button on the first or second side of the device, by which the caregiver can either input a specific time for an alarm in Set [Clock] mode or specific number of minutes or hours for the alarm in Set [#] mode. For example, the alarm can be set for 2:25 pm or in 3 hours, respectively; a Light switch/button on the face or a side of the device and a USB port for data transfer and/or, optionally, a WiFi switch/button on a side of the device serving for data transfer.

DETAILED DESCRIPTION OF THE INVENTION

Figure 1A:
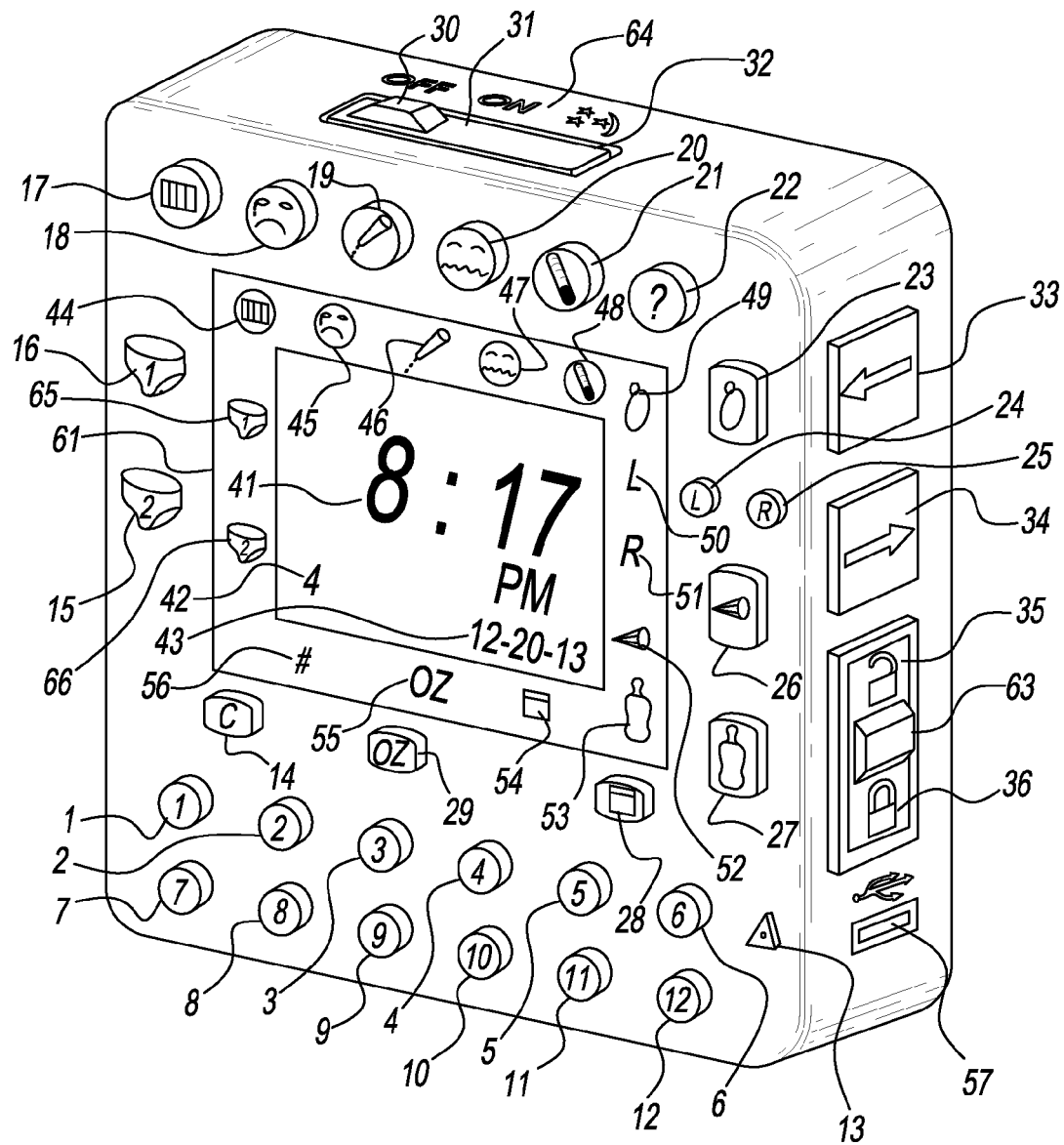
FIG. 1A illustrates a perspective view of the preferred embodiment of the present invention.

Hereinafter, selected examples and operating functions of a multi-event time and data tracking device dedicated to baby care will be discussed in the following with reference to the accompanying drawings FIG. 1A, FIG. 1B and FIG. 2. It will be appreciated by those skilled in the art that the following discussion is for illustration purposes only and should not be interpreted in limitation of the invention. Other variances within the scope of this disclosure are also applicable.

"Optional" or "optionally" means that the subsequently described circumstance may or may not occur, so that the description includes instances where the circumstance occurs and instances where it does not.

More specifically, the invention is directed to a battery operated device for tracking baby care in the present invention, comprising: an information screen 61 on the face of the device displaying the current date 43 and time 41 in one mode as well as the time since and number of the last inputted event 42, 56 for baby care categories in another mode and even more specific information for various baby care events in other corresponding modes;

a first group of buttons 1-12 on the same face of the device, labeled as integers of 1-12 as well as a Clear button 14 and a Decimal point button 13, wherein the first group of buttons are situated in one or more rows parallel to the longest dimension of the information screen;

a second group of buttons 23-28 brightly and differently colored and/or illuminated for easy identification, on the same face of the device, labeled as baby feeding events, including nursing, pumping, bottle feeding and baby food feeding, wherein the second group of buttons are placed in one row and one column, parallel and perpendicular to the first group of buttons. Furthermore, included to the side of this group of buttons, are a L 24 for left breast and R 25 for right breast or a symbol equivalent to the left or right breast for nursing and pumping modes;

a third group of buttons 15-22 on the same face of the device, brightly and differently colored and/or illuminated for easy identification, on the same face of the device, labeled as baby care events, including wet and/or soiled diapers, sleeping, crying, medication, vomiting, temperature and a generic event; wherein the third group of buttons are placed parallel to the first group of buttons.

a fourth group of buttons 33-34 on the face or side of the device serving as scan buttons, wherein at least two scan buttons are arranged in one row or column which is parallel or perpendicular to the first group of buttons;

an Alarm switch/button 62 on the face or side of the device;

a Lock and Unlock switch/button 63 on the first or a second side of the device;

a Light switch/button 64 on the side or face of the device; and a USB port 57 on a side of the device serving for data transfer.

Referring to FIG. 1A, the information screen 61 is situated in the middle to upper portion of the face of the device. The information screen has peripherals parallel to the edges of the device. When the device is in active use or in the Unlocked mode 35, a caregiver is either inputting or reviewing a data entries and the information screen displays the intended information or numbers with the corresponding icons 44-54 associated with the particular baby care event being reviewed or recorded. When the device is not in active use or in the Locked mode 36, the information screen 61 displays the date 42 and time 41 with an am and pm indicator 41. The information screen 61 can be a LCD display, Electroluminescence display, or an e-ink display or OLED display. The display can be either a black/white display or a colored display. In addition, the numbers in the display can be illuminated 32 with a colored backlight or backlights for the caregiver to easily use and read the device at night. Also, data and times for different categories of baby care events can be illuminated in different colors to make their recognition easier.

The buttons from the first to the fourth groups are data entry or data review buttons. Data entry includes baby care event entry 17-28 and numerical data entry 1-12. The icons labeled on the buttons from the first to the fourth groups are intended to use universal symbols so that people from different countries and cultures can easily understand and use the device. This can be useful not only for non-English speaking caregivers during everyday use but also particularly beneficial for international travel or emergency situations.

Referring to FIG. 1A, the first group of the buttons 1-12 are labeled or displayed as integers from 1 to 12. The number buttons are arranged in one or more rows or columns. Preferably, the numbers are arranged in two rows. Further, a Decimal point 13 is labeled on a button located very close to the first group of buttons. Optionally, there is no decimal point button but just a static decimal point permanently set on the screen which will serve as a decimal point to the hundredth place for partial amounts and temperatures as well as being substituted as a colon for the input of specific times. A Clear C 14 or erase button is placed in close proximity to the number buttons. The numbers are used to input numbers in various baby care events. The Decimal point is used to input portion ounces and minutes in an alarm mode. Clear button or a symbol such as the letter C is used to erase any inputting errors.

The second group of buttons 23-28 are brightly colored and/or illuminated for easy identification on the same face of the device and labeled as baby feeding events. The baby feeding events include, but are not limited to, a button associated with nursing 23 like the symbol of a baby in a mother's arms or an icon indicating the same, a button associated with pumping 26, such as the symbol of a funnel or letter P or an icon indicating the same, a button associated with bottle feeding 27, such as a symbol of a milk bottle or a icon suggesting the same, and a button associated with baby food feeding 28, such as a symbol of a baby food jar or anything else that can be interpreted as the same. The second group of buttons can be arranged in one or more rows or columns. Preferably, the baby feeding buttons are arranged in one row and column, as indicated in FIG. 1A. In addition, the baby feeding buttons are placed close to the first group of number buttons so that the caregivers can easily locate them.

Furthermore, the second group of the baby feeding buttons have two additional buttons, 24-25, labeled L for Left breast and R for Right breast. The L 24 and R 25 are placed right next to the other baby feeding buttons, particularly the buttons associated with nursing and pumping. The L and R buttons allow the parent to designate the breast for feeding or pumping for each feeding session as they desire.

The first and second groups of buttons are preferably located on the bottom and to the side of the display screen, allowing the caregiver to comfortably view the information screen while inputting the information.

The third group of buttons 15-22 are brightly colored and/or illuminated for easy identification on the same face of the device and labeled as baby care information. The colors of the buttons can also be representative of their function to further facilitate easy input and access. For example, the diaper button #1 16 can be yellow and button #2 15 brown, representing urine and feces respectively, the temperature button 21 can be red, representing a fever and the vomiting button 20 can be green, representing nausea. In addition, symbols or icons on the buttons are associated with various unique baby care events. The baby care events include, but are not limited to, wet 16 and/or soiled 15 diapers or symbols of a number 1 16 and number 2 15 on a triangular buttons or an equivalent, sleeping 17 or a symbol of a crib or an equivalent, crying 18 or a symbol of sad face with tears or an equivalent, medication 19 or a symbol of a dropper or an equivalent, vomiting 20 or a symbol of a nauseated face or an equivalent, temperature 21 or a symbol of a thermometer or an equivalent and a generic event 22 or a symbol of a question mark or an equivalent.

The fourth group of buttons 33-34 serve as scan buttons to access and track information in chronological order in any baby care event category.

The buttons with icons can be located either above the information screen or next to the information screen. Referring to FIG. 1A, the baby care event buttons are conveniently located either above or next to the side of the information screen for easy data input.

Each unique baby care event can be recorded by first moving the switch from the Locked position to the Unlocked position. The caregiver then presses any baby care event button 17-28 on the face of the device. Then the information display will show the icon 44-54, 65-66, associated with that event along with the 56 and chronological number 42 assigned to the last data entry for that baby care category in the current 24 hour timeframe. In addition, all number buttons 1-12 that have already been used to record information in a 24 hour period for a particular category of baby care will be illuminated and the number of the last illuminated button will be displayed on the screen to indicate the chronological number of the last event. This indicates to the parent that the next unlit number is the number to be pressed to record the start of the current event. The same number button, now backlit, is to be pressed again to record the end and duration of the current event.

In the preferred embodiment of the device, when the switch is in the Lock position 36 and the caregiver presses any baby care event button 17-28, she is able to see the time since and chronological number 42, 56 of the last inputted data for any baby care event on the device's information screen.

The Lock switch 36, on the right side of the face of the device comprises a Lock and Unlock mode. The Lock mode is placed as a necessary feature to avoid accidental data input while the device is not in active use and to allow caregivers or medical professional to instantly review the most recently inputted data by pressing any single baby care event button 17-28.

The device further comprises a Light mode 64 on the top side of the device. In one example of the present invention, when the Light switched is moved from the Off position 30 to the On position 31, the information screen and all buttons will be illuminated with a bright backlight, which could also be used as a temporary nightlight by a parent to navigate their way through the dark. In another example, when the Light switch is moved the Nighttime Illumination position 32, the screen and buttons on the device will become dimly lit anytime a parent touches any button or switch so the baby is not disturbed by a bright light. In the Nighttime illumination mode, the light will automatically shut off after a predetermined time of inactivity to a sleep mode to save battery energy.

The baby care events 17-28 are referred to as events or categories in the present invention. Each baby care category can be labeled or displayed in either word or icon forms and has a corresponding icon 44-54 on the information screen. For example, the icon or symbol associated with pumping can be labeled using word "pumping" or any symbol suggesting the same just as the icon for volume/amount 55 can be labeled using the abbreviation of the word ounce or OZ 29 or label or word clearly indicating the same.

When a mother wishes to pump milk or feed her baby, she first unlocks the device then presses a button from group of pumping or baby feeding buttons 49-54, including nursing 23, pumping 26, bottle feeding 27 and baby food feeding 28. Once a particular type of baby feeding event button is pressed, the icon for that event will appear on the information screen and the caregiver can continue to press the button immediately after the last illuminated number button to record the start time for the feeding and then press the same button, which is now also illuminated, again to indicate end of the feeding.

If the caregiver is the mother, further selection of the L 24 or R 25 buttons indicating the left or right breast for nursing or pumping can be inputted into the device after the corresponding number button for the event is pressed. To clarify which number of daily feedings or other baby care events 17-28 the baby is up to in 24 hour timeframe, only the previously pressed number buttons will be illuminated when the device is backlit and the chronological number of the last illuminated number button, indicating the last feeding, will be displayed in the lower left side of the information screen 42.

When the mother finishes pumping or feeding her baby, she may choose to press OZ button 29 to record the amount consumed or pumped. The caregiver can then proceed to input the number of ounces that the baby consumed or mother pumped for the feeding/pumping by using the number buttons 1-12 and Decimal point button 13 to record partial ounces.

Optionally, the amount of mother's milk a baby takes in a nursing mode can also be retrieved by weighing the baby and recording the weight before and after the nursing session and record the difference into the device.

The mother may also want to use the duration of and which breast was used for a nursing session to track trends in nursing data which can indicate a milk supply problem for the mother.

In the preferred embodiment of the invention, the OZ or ounce button 29 can be pressed immediately after any other baby care event as well. Its function is not limited to feeding events.

In the preferred embodiment of the invention, if the baby needs to be administered medications, such as infant Zantac for Gastroesophageal reflux disease, on a regular basis or when the baby is sick and a certain medication is administered, to record the time the medication was administered, the caregiver will first move the Lock switch 35 on the side of the device to the Unlock position 36, then she should press the Medication button 19, labeled as a dropper or other universally understood icon and lastly she must press the number button 1-12 after the last illuminated number, also indicated by number 42 displayed on the information screen.

In the preferred embodiment of the invention, the caregiver can then input into the device how much medication the baby has taken by using a combination of the OZ button and number buttons in fashion similar to the recording of the volume of a feeding. For example, if a mother would like to record the amount of medication her baby was just administered, 1.25 ounces, she would press the OZ button 55 immediately after pressing the number button to record the time of the medication administration. After pressing the OZ button, the mother will simply input the number of ounces of medication using the number buttons 1-12. For instance, if she would like to record 1.25 ounces, she would press the 1 button 1, then the Decimal button 13, then the number 2 button 2, then the number 5 button 5 and if she had no other events to record she would slide the switch back to the Lock position.

The present invention further allows for a recording of a number of medications. When the device is in the Unlock position 35 and the Medication button 19 is pressed, the parent can then press either scan button 33-34 to scroll through the different numbers the parent has assigned to different medications. After the desired medication is found, the parent presses the Medication 19 button again and follows with pressing the corresponding chronological number button 1-12 to record the time of the administration of that particular medication.

To record the time and duration of a nap, a parent must unlock the device, then press the Crib icon button 17 and the number button after the last illuminated button to begin recording the nap and then must press the same button, which is now illuminated, when the baby wakes up. To review how long it has been since the baby woke up from his last nap, the caregiver simply pushes the Crib button 17 while the device is locked and the time appears along with the chronological number for that nap in the current 24 hour time period.

Episodes of crying are recorded and reviewed in the same fashion as the naps but with using the Crying button 19 and icon 45.

To record the time and number of times an infant vomits, the caregiver will unlock the device and press the Vomiting button 20 and then the first unlit number from the number buttons 1-12 for each incident of vomiting that occurs. This baby care event is represented by a nauseated-looking face 20, 47 in the present embodiment but can be represented as anything depicting the same.

To record the time and temperature readings of an infant, the parent will unlock the device and press the Temperature button 21 then the first unlit number button 1-12 to record the time of the reading and then to record the reading itself, the caregiver will use the same number buttons 1-12 along with the Decimal point button 13. Temperature 21, 48 is represented as a thermometer in the present embodiment but can be represented as anything depicting the same.

In the preferred embodiment, there is also a button 22 and screen display icon for a generic event represented as a question mark or anything indicating the same.

The data collected from using the baby care event buttons together can provide useful routine information for a parent about the general wellbeing of a baby. However, the present invention also allows a caregiver to identify abnormal baby behavior early and seek medical help. In addition, the combination of medication information and diaper information can provide critical feedback for doctors to review in babies with GI tract, kidney and renal diseases.

Figure 1B:
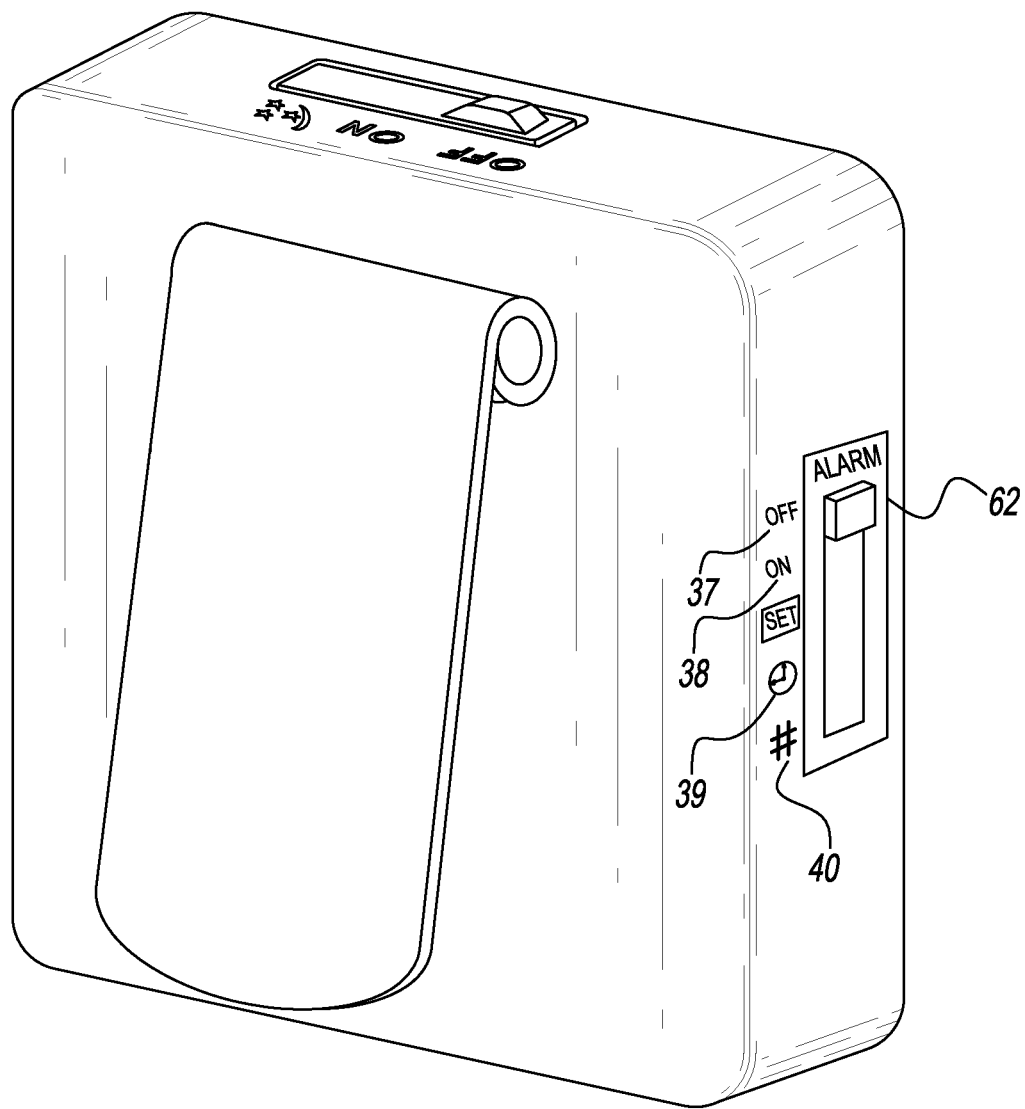
FIG. 1B illustrates a perspective view of the first side and back of the present invention containing the alarm switch and clip.

Referring to FIG. 1B, the device further comprises an Alarm mode 62, accessed by a switch/button on the left side of the device, to remind the caregiver of the next baby care event by either an audible alarm and/or vibration, both types of alarms can be accompanied by the backlight being lighted as well. The On 38 and Off 37 status of the alarm can be set by moving the switch to the corresponding On 38 and Off 37 position on the left side of the device. The alarm status can be set or reset by first having both the Alarm switch set to either the Clock icon 39 or Number icon 40 modes and by pressing the button for the baby care event for which the caregiver would like to set the alarm. The caregiver can either input a specific time for an alarm in the Set [clock] mode 39 such as 3:10 am using the number buttons 1-12 and/or the caregiver can input a specific number of minutes or hours for the alarm to go off in the Set # mode 40. For example, the Alarm can be set to go off in 2 hours. The caregiver will also have the option to set the Alarm to go off repeatedly at specific times or for specific durations of time. Again, the detailed time for being alarmed at, including hours and minutes, can be set by using the number buttons 1-12 and decimal point button 13, to indicate a colon, in the first group of buttons.

Figure 2:
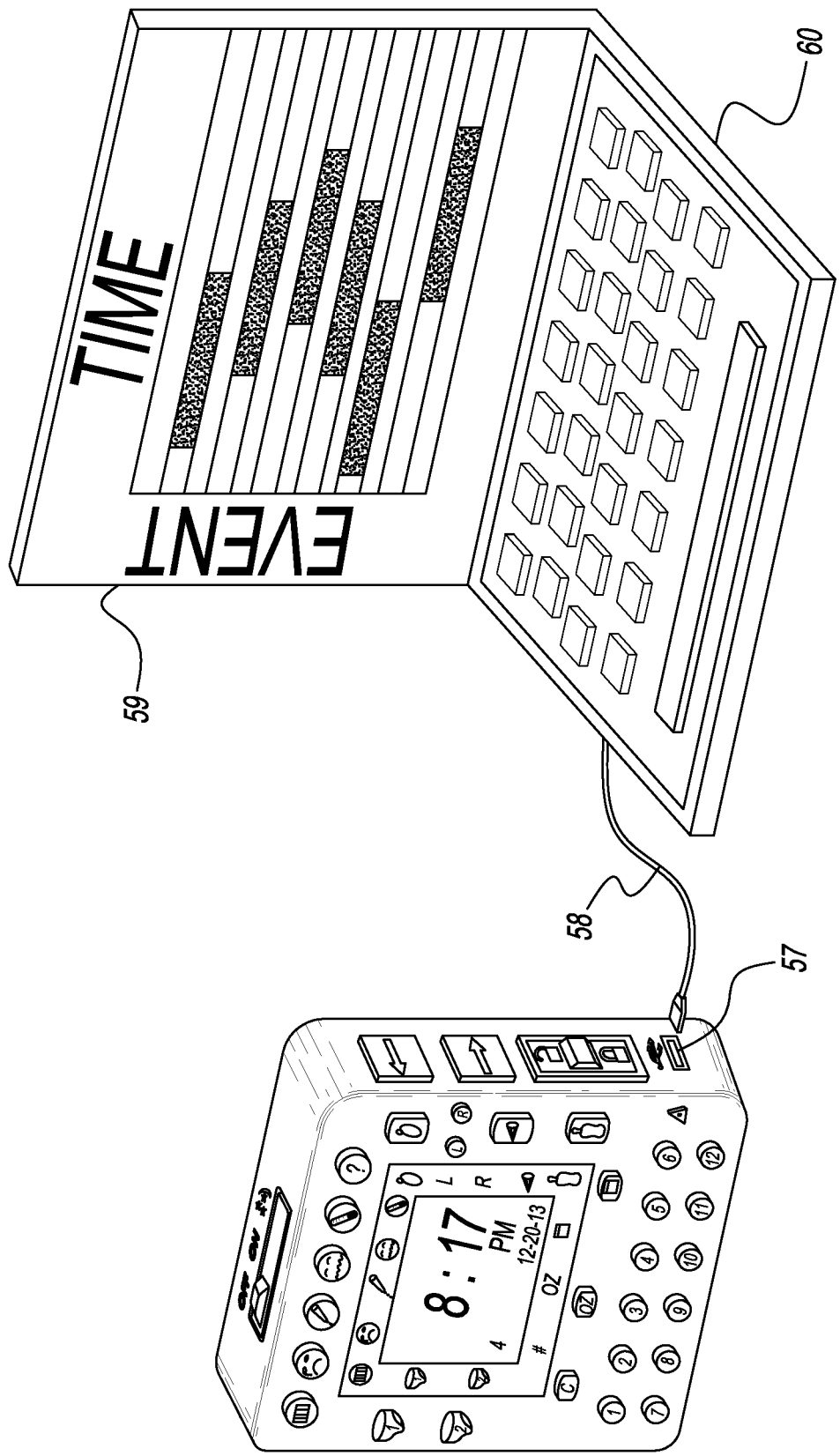
FIG. 2 illustrates a representation of the downloading function of the present invention.

Referring to FIG. 2, in accordance with other aspects of the present invention, the device has a USB port 57 to facilitate data transfer. The caregiver can download using a USB cord 58 all the information from the device to a computer/phone/tablet 60, from a temporary memory in the device to a more permanent memory external to the device. The information can further be organized in a chart and or graph 59 by an application or software associated with the computer, phone or tablet. The chart can be emailed or printed to be discussed with a pediatrician during medical check-ups and sick visits.

The preferred embodiment of the device also comprises a communication means to interface with an external computing device, said external computing device being capable of viewing and extracting information from the device in the present invention. In one example, the device further comprises WiFi abilities and can be synchronized with the iPad, iPhone or other computing/information storage devices. Optionally, the device can further be tracked for its location.

Optionally, the device comprises a touchpad or touch screen to input and access data.

Optionally, the device comprises a video screen and/or audio monitoring system capable of wireless transmission of images and audio from a camera and/or audio receiver in the baby's room.

Intrinsically, an operable device described in the present invention requires a microprocessor to compile the information input and store in a temporary storage for further data transfer or manipulating. The microprocessor may comprise a microcontroller to respond when a different operation mode, or baby care event button, is selected and a memory storage to communicate with the microcontroller and/or external device.

The device can be made in different shapes, with ergonomic features or easy to grab onto features. Preferably, as illustrated in FIG. 1A, the device is rectangular in shape. In one example the device has a dimension of 3.5 inches. In another example the device has a dimension of 3 inches. In still another example, the device is 3.5 inches×3 inches.

Referring to FIG. 1B, the device is intended to have maximum portability. In one example, the device has a durable metal and/or plastic clip on the back which the caregiver can adjust to prop up the device on a table or flat surface. In another example, the caregiver can wear the device on her belt/pants. In another, a comfortable cord/fabric is fastened to the device so that it can be worn around a caregiver's neck to maximize portability.

In accordance with the present invention, the device is battery operated. Optionally, the device's battery has a plug-in rechargeable function to enable quicker recharge if a battery replacement or recharge is not immediately available.

Preferably, the device is also lightweight.

We claim:

1. A battery operated multi-event data and time tracking device for monitoring baby care comprising:
    a plurality of buttons on the face of the device, grouped together and labeled with integers 1-12, which instantly indicates the aggregate number of instances of a particular baby care event for a period of time, through the simultaneous illumination of the integer buttons and a numerical display on an information screen;
    a plurality of labeled buttons on the face of the device, grouped together and brightly colored to represent their functions, wherein each button accesses a different event or mode of baby care, including wet and/or soiled diapers, sleeping, crying, medicine administration, vomiting, temperature, nursing and pumping from the left and/or right breast, bottle feeding, baby food feeding and a generic event, with all buttons and switches having corresponding representation in iconic form on the information screen and when pressed will become illuminated in combination with the corresponding illumination of a number button or buttons from 1-12 for an instant visual computation of aggregate data for a particular baby-related event;
    a clear button, a decimal point button and scanning arrow buttons;
    an alarm switch, a lock switch and a lighting control switch;
    an information screen on the face of the device, displaying temporal and numerical data in various modes with respect to particular baby care events,
    a microprocessor for providing temporary memory storage for the device and mode selection and data input for each of the buttons as well as allowing wireless transmission of data to permanent memory of another computing device; and
    a USB port on a side of the device for data transfer from the microprocessor's temporary memory storage to the other computing device's permanent memory storage for the purpose of having the data organized in a graphic format to facilitate the functional analysis of infant behaviors and comparison of behavior trends based on the frequency, duration, temporal data and simultaneous occurrences of behaviors.

2. The device of claim 1, wherein it has dimensions of a hand-held device to facilitate portability.

3. The device of claim 1, wherein it has a durable metal and/or plastic clip on the back thereof so it can be adjusted to be propped up on a table or other flat surface.

4. The device of claim 1, wherein it has a durable metal and/or plastic clip on the back thereof so it can be adjusted to be worn on a belt or pair of pants.

5. The device of claim 1, wherein it has a durable metal and/or plastic clip on the back thereof so it can be adjusted to be fastened to a comfortable cord or loop allowing it be worn around the neck.

* * * * *